United States Patent
Nakamura et al.

(10) Patent No.: US 6,936,659 B2
(45) Date of Patent: Aug. 30, 2005

(54) POLYMER-BONDED FUNCTIONAL AGENTS

(75) Inventors: Michiei Nakamura, Tokyo (JP);
Hiromitsu Yanagimoto, Tokyo (JP);
Hiroyuki Shimanaka, Tokyo (JP);
Rokuya Yamashita, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 10/201,151

(22) Filed: Jul. 24, 2002

(65) Prior Publication Data

US 2003/0078346 A1 Apr. 24, 2003

Related U.S. Application Data

(62) Division of application No. 09/611,341, filed on Jul. 6, 2000, now abandoned.

(30) Foreign Application Priority Data

Jul. 7, 1999 (JP) ............................................. 11-193039

(51) Int. Cl.⁷ ............................................. C08L 39/04
(52) U.S. Cl. ......................................... 525/61; 525/204
(58) Field of Search ................................... 525/61, 204

(56) References Cited

U.S. PATENT DOCUMENTS

| | | |
|---|---|---|
| 3,337,288 A | 8/1967 | Horiguchi et al. |
| 3,344,098 A | 9/1967 | Horiguchi et al. |
| 3,457,328 A | 7/1969 | Blatz |
| 3,462,388 A | 8/1969 | Horiguchi et al. |
| 3,467,642 A | 9/1969 | Horiguchi et al. |
| 3,563,931 A | 2/1971 | Horiguchi et al. |
| 3,637,581 A | 1/1972 | Horiguchi et al. |
| 3,640,983 A | 2/1972 | Horiguchi et al. |
| 3,825,523 A | 7/1974 | Iwata et al. |
| 3,926,830 A | 12/1975 | Horiguchi et al. |
| 4,213,892 A | 7/1980 | Scott |
| 4,221,700 A | 9/1980 | Minagawa et al. |
| 4,520,171 A | 5/1985 | Diveley et al. |
| 4,528,311 A * | 7/1985 | Beard et al. ................... 524/91 |
| 4,857,596 A | 8/1989 | MaCLEAY et al. |
| 4,863,999 A | 9/1989 | MaCLEAY et al. |
| 4,866,136 A | 9/1989 | MaCLEAY |
| 5,112,912 A | 5/1992 | Nikles |
| 5,538,519 A | 7/1996 | Horiguchi et al. |
| 6,001,337 A | 12/1999 | Keller et al. |
| 6,008,302 A | 12/1999 | Olson et al. |
| 6,147,170 A * | 11/2000 | Hofmann ..................... 525/539 |

FOREIGN PATENT DOCUMENTS

WO     WO 98/18830     7/1998

OTHER PUBLICATIONS

Whelan, "Polymer Technology Dictionary", 2$^{nd}$ ed., Chapman & Hall, New York, p. 295 (1994).*

\* cited by examiner

*Primary Examiner*—Bernard Lipman
(74) *Attorney, Agent, or Firm*—Oblon, Spivak, McClelland, Maier & Neustadt, P.C.

(57) ABSTRACT

Polymer-bonded functional agents are each obtained by reacting a functional agent containing reactive groups with a polymer containing groups reactive with the reactive groups of the functional agent. The functional agent comprises at least one functional agent selected from the group consisting of antioxidants, ultraviolet absorbers, light stabilizers, infrared absorbers and antistatic agents. Use of these polymer-bonded functional agents can provide articles with improved functions.

6 Claims, No Drawings

POLYMER-BONDED FUNCTIONAL AGENTS

This application is a divisional application of U.S. Ser. No. 09/611,341, filed Jul. 6, 2000, now abandoned.

BACKGROUND OF THE INVENTION a) Field of the Invention

This invention relates to polymer-bonded functional agents, and more specifically to polymer-bonded functional agents with an antioxidant, an ultraviolet absorber, a light stabilizer, an infrared absorber and/or an antistatic agent contained therein as a functional agent in a bonded form. The present invention is also concerned with processes for the production of the polymer-bonded functional agents, polymer-bonded functional agent compositions, processing methods for improving functions, and articles or products with improved functions.

a) Description of the Related Art

Synthetic resins, natural resins and semisynthetic resins (hereafter simply called "resins") are accompanied by a problem in that they undergo a thermal deterioration under heat upon molding, forming or the like, an oxidative deterioration by oxygen in air when used or stored over long time, or a reduction in elasticity, a reduction in tensile strength, a reduction in physical properties, such as development of cracks, a deterioration in electrical properties, coloration and/or the like due to embrittlement or the like under the action of sunlight, especially ultraviolet rays. Likewise, products which contain a resin as an essential component—such as coating materials, paints, offset inks, gravure inks, textile printing inks—also develop a quality deterioration such as a gloss reduction, crazing or cracking, or blister of resin coatings or discoloration or fading of a pigment.

To lessen the above-described problems, antioxidants, for example, hindered phenolic antioxidants, phosphorus-containing antioxidants, sulfur-containing antioxidants and the like have been used commonly for oxidative deteriorations of resins. To avoid discoloration, embrittlement or the like of resins by ultraviolet rays, gloss reductions, crazing or cracking or blister of resin paints, or discoloration or fading of dyes or pigments, on the other hand, ultraviolet absorbers, especially benzotriazole ultraviolet absorbers, triazine ultraviolet absorbers, salicylate ultraviolet absorbers, benzophenone ultraviolet absorbers and the like have been used, or light stabilizers such as those of the hindered amine type have been used in combination with the above-described antioxidants and/or ultraviolet absorbers. Further, antistatic agents have also been used to prevent electrification.

Use of functional additives (functional agents) such as the above-described antioxidants, ultraviolet absorbers, and light stabilizers, however, develops various inconvenience because they are generally compounds of low molecular weight. For example, a functional agent of relatively low boiling point or a sublimable functional agent undergoes evaporation, sublimation or the like when a resin is molded, formed or otherwise processed under heat or is cured under heat. When a resin product or resin coating is brought into contact with warm water or an aqueous, acidic or alkaline solution or an organic solvent such as an alcohol or oil, the functional agent in the resin product is extracted from the resin. As a consequence, it is impossible to allow the effect of the functional agent to last for long time.

When a functional agent is mixed with a resin, poor compatibility between the functional agent and the resin causes bleeding or blooming on a surface of a molded or otherwise formed product of the resin or on a surface of a coating on the product during its long-term use. A problem, therefore, arises in that the content of the functional agent becomes low or that in the case of an adhesive or printing ink containing the resin, adhesion or printability may be lowered or the functional agent bled out onto the surface may stain other product(s) and/or article(s). On the other hand, addition of a functional agent in a large amount to a resin causes a phase separation between the resin and the functional agent, leading to reductions in the transparency and mechanical strength of the resin. A limitation is therefore imposed on the amount of the functional agent to be added. There has hence been a demand for the elimination or lessening of these problems. Further, a functional agent is generally a low molecular compound so that, when the functional agent adheres to the human body, it may cause irritation to skin or mucosa depending upon its type. In addition, powdery functional agents include those requiring attention from the standpoint of safety and/or health, for example, to the production of dust.

Some attempts have, therefore, been made to prevent evaporation, leaching or the like of an ultraviolet absorber when the ultraviolet resin is added to a resin. According to these attempts, one or more (meth)acryloyl groups are introduced into the ultraviolet absorber, and the resulting (meth)acryloyl-containing ultraviolet absorber is copolymerized as a monomer with another monomer so that the ultraviolet absorber is provided with a high molecular weight. In general, however, it has been difficult to prevent gradual polymerization of these (meth)acryloyl groups during storage. There is also a practical problem. A copolymer, which is available as described above, is a copolymer with another vinyl monomer such as an acrylic compound, a methacrylic compound, styrene or vinyl acetate. A limitation is hence imposed on the range of applicable resins because, for example, the thus-copolymerized ultraviolet absorber may not have sufficient compatibility with certain kinds of principal resins, e.g., polyolefin resins such as polyethylene and polypropylene, various polyester resins, diverse polyamide resins, and various polycarbonate resins. As physical property improvers for a wide range of general-purpose resins, the above-described problems still remain unsolved.

SUMMARY OF THE INVENTION

The present inventors have proceeded with extensive research to solve or lessen the above-described problems. As a result, it was found that these problems can be solved or lessened by a polymer-bonded functional agent which is available by bonding an antioxidant, ultraviolet absorber, light stabilizer, infrared absorber or antistatic agent, which contains a reactive group, preferably, a condensation- or addition-reactive group, to a polymer, which contains groups reactive with the above-mentioned reactive groups, through a reaction, preferably, a condensation or addition reaction. The present invention has been completed based on this finding. Namely, the selection of a functional agent and a polymer, which are reactive with each other, upon production of a polymer-bonded functional agent, makes it possible to obtain the polymer-bonded functional agent as a functional agent suitable for a resin or the like to which the polymer-bonded functional agent is added. Further, compared with conventional functional agents, the polymer-bonded functional agent according to the present invention has better compatibility with various resins and is also superior in physical properties such as thermal stability and bleed resistance.

Described specifically, the present invention therefore provides a polymer-bonded functional agent obtained by reacting a functional agent containing a reactive group with a polymer containing groups reactive with the reactive groups of the functional agent (hereinafter "polymer" may be referred to as "resin"), wherein the functional agent comprises at least one functional agent selected from the group consisting of antioxidants, ultraviolet absorbers, light stabilizers, infrared absorbers and antistatic agents; its production process; a method of its use; and a product making use of the same.

The polymer-bonded functional agent according to the present invention can be obtained by reacting the functional agent, which contains the reactive group, with the polymer, which contains the groups reactive, preferably, condensation- or addition-reactive with the reactive groups of the functional agent, and bonding the functional agent and the polymer through covalent bonds. This condensation or addition reaction can be applied to a wide variety of polymers including polyolefins. According to the present invention, the content of the functional agent in the polymer-bonded functional agent can be easily controlled. In particular, one containing a functional agent at a high content can be synthesized with ease. Further, the polymer and functional agent, which are used as starting materials, or their intermediates can be easily synthesized or are readily available. As condensation- or addition-reactive groups stably remain over long time in many instances, it is possible to produce beforehand these starting materials in large amounts and to synthesize the polymer-bonded functional agent in desired amounts whenever needed.

As a physical property deterioration improver for resins and resin-base coating materials, the polymer-bonded functional agent according to the present invention has excellent compatibility with the resins and resin-base coating materials in which the polymer-bonded functional agent is to be used. When a molded or otherwise formed product is produced under heat from a resin which contains the polymer-bonded functional agent according to the present invention or when the polymer-bonded functional agent according to the present invention is used in a coating material, paint, ink or the like and the coating material, paint, ink or the like is then hardened under heat, the functional agent remains free from vaporization through evaporation or sublimation. Further, the functional agent is free from dissolution or leaching into water or organic solvents so that the polymer-bonded functional agent does not cause bleedout of the functional agent onto a surface of the molded or otherwise formed product or onto a surface of a coating on the molded or otherwise formed product. As the functional agent is-bonded with the polymer of high molecular weight in the polymer-bonded functional agent according to the present invention, the polymer-bonded functional agent is also excellent in safety and health.

DETAILED DESCRIPTION OF THE INVENTION AND PREFERRED EMBODIMENTS

The present invention will hereinafter be described in more detail based on certain preferred embodiments.

The functional agent containing a reactive group and used in the present invention is at least one functional agent selected from the group consisting of antioxidants, ultraviolet absorbers, light stabilizers, infrared absorbers and antistatic agents.

The reactive group of the functional agent and those of the polymer can be selected as a combination of mutually-reactive groups selected, for example, from the group consisting of hydroxyl groups, carboxyl groups, acid halide groups, acid anhydride groups, lower ($C_1$–$C_3$) alkyl ester groups, epoxy groups, amino groups, chlorotriazine groups, isocyanate groups, like a combination of hydroxyl groups and isocyanate groups.

Usable as the functional agent containing a reactive group is a derivative obtained by introducing the above-described reactive group in a known functional agent. Illustrative antioxidants can include derivatives of hindered phenolic antioxidants, such as 3-(3',5'-di-t-butyl-4'-hydroxy-phenyl) propionic acid, 3-(3'-t-butyl-5'-methyl-4'-hydroxy-phenyl) propionic and the like, and their acid chlorides; and derivatives of sulfur-containing antioxidants such as monododecyl 3,3'-thiobispropionate, monooctadecyl 3,3'-thiobispropionate, and their acid chlorides.

Illustrative ultraviolet absorbers can include derivatives of benzotriazole ultraviolet absorbers, such as 3-[3'-(2"H-benzotriazol-2"-yl)-4'-hydroxyphenyl]propionic acid, 3-[3'-(2"H-benzotriazol-2"-yl)-5'-methyl-4'-hydroxyphenyl] propionic acid, 3-[3'-(2"H-benzotriazol-2"-yl)-5'-ethyl-4'-hydroxyphenyl]propionic acid, 3-[3-(2"H-benzotriazol-2"-yl)-5'-t-butyl-4'-hydroxyphenyl]propionic acid, 3-[3'-(5"-chloro-2"H-benzotriazol-2"-yl)-5'-t-butyl-4'-hydroxyphenyl]propionic acid, 3-[3"-(2"'H-benzotriazol-2"'-yl)-4"-hydroxy-5"-(1',1'-dimethybenzyl)phenyl] propionic acid, 3-[3"-(2"'H-benzotriazol-2"'-yl)-4"-hydroxy-5"-(1",1",3",3"-tetramethylbutyl)phenyl]propionic acid and the like, and their acid chlorides.

Examples of other ultraviolet absorbers can include derivatives of triazine ultraviolet absorbers, such as 2-[4'-[(2"-carboxypropioxy-3"-dodecyloxypropyl)oxy]-2'-hydrophenyl]-4,6-bis(2',4'-dimethylphenyl)-1,3,5-triazine, 2-[4'-[(2'-phthalyloxy-3'-dodecyloxypropyl)oxy]-2'-hydroxy-phenyl]-4,6-bis(2',4'-dimethylphenyl)-1,3,5-triazine and the like, their dicarboxylic acid half ester derivatives, and their acid chlorides; benzoic acid ultraviolet absorbers such as benzoic acid, p-aminobenzoic acid and p-dimethylaminobenzoic acid, cinnamic acid ultraviolet absorbers such as cinnamic acid and p-methoxycinnamic acid, salicylic acid, and the like; and their acid chlorides.

Examples of light stabilizers can include derivatives of hindered amine light stabilizers, such as 2,2,6,6-tetramethyl- 4-piperidinol, 1,2,2,6,6-pentamethyl-4-piperidinol and the like, their dicarboxylic acid half ester derivatives, and their acid chlorides. Examples of ultraviolet absorbers can include derivatives of infrared absorbers, such as tris(t-octyl-naphthalo)(carboxyl-phthalo)cyanine-vanadium oxide complex and N-(o-carboxyl-p-dibutylaminophenyl)-N,N', N'-tris(p-dibutylaminophenyl)-p-phenylenediamine hexafluorophosphate.

Examples of antistatic agents can include derivatives of antistatic agents, such as polyethylene glycolmonomethyl ether, poly(ethylene glycol-propylene glycol) monomethyl ether, poly(ethylene glycol-propylene glycol)monobutyl ether, N,N-diethylaminoethanol, N,N-diethylaminopropanol, N,N-diethylaminoethoxy-polyethylene glycol and the like, their dicarboxylic acid half ester derivatives, and their acid chlorides; 3-diethylaminopropionic acid, 2,3-epoxypropyl-dimethylamine, and 2,3-epoxypropyl-trimethylammonium chloride.

Illustrative of the polymer containing the groups reactive, preferably condensation- or addition-reactive with the groups of the functional agent are polyolefin polymers such as polyethylene, polypropylene, poly(ethylene-propylene) and poly(ethylene-propylene-α olefins); polyether polymers such as polypropylene glycol, poly(ethylene glycol-propylene glycol), (polyethylene glycol)-(polypropylene glycol) block copolymer and polytetramethylene glycol; aliphatic polyesters such as polybutylene adipate and polyethylene sebacate; polyesters, for example, aromatic polyesters such as polyethylene isophthalate, polybutylene terephthalate and polyneopentyl terephthalate; polyamides such as 6-nylons and 6,6-nylons; polyvinyl polymers such as polystyrene, styrene copolymers and polyvinyl butyral; (meth)acrylic (co)polymers such as acrylate ester (co)polymers, methacrylate ester (co)polymers and acrylic compound-styrene copolymers; polysilicone polymers; polyurethane resins; polyurea resins; epoxy resins; melamine resins; cellulose resins; chitosan resins; copolymers of two or more of the monomers making up the above-described polymers; and block copolymers formed of two or more of the above-described polymers.

When expressed in terms of number average molecular weight range, the polymer which is reacted with the functional agent can be a polymer having a molecular weight on the order of from about 3,000 to about 200,000, preferably from about 5,000 to about 100,000.

The reactive groups of the polymer which is reacted with the functional agent can be those condensation- or addition-reactive with the reactive groups of the functional agent and selected from the group consisting of known reactive groups such as hydroxyl groups, carboxyl groups, acid halide groups, acid anhydride groups, lower ($C_1$–$C_3$) alkyl ester groups, epoxy groups, amino groups, chlorotriazine groups, isocyanate groups. The preferred combination of the reactive groups of the functional agent and those of the polymer can be a combination of hydroxyl groups or carboxyl groups and carboxylic acid chloride groups.

Preferred examples of the polymer having the above-described reactive groups can include, as reactive polyolefins, poly(ethylene-vinyl alcohol) copolymer, poly(ethylene-vinyl alcohol-vinyl acetate) copolymer, poly(ethylene-acrylic acid) copolymer, poly(ethylene-methyl acrylate) copolymer, poly(ethylene-methacrylic acid) copolymer, poly(ethylene-methyl methacrylate) copolymer, poly(ethylene-vinyl alcohol-methacrylic acid) copolymer, poly(ethylene-ethyl acrylate-maleic anhydride) copolymer, poly(ethylene-butyl acrylate-maleic anhydride) copolymer, polyethylene-maleic anhydride graft copolymer, poly(ethylene-glycidyl methacrylate) copolymer, polyethylene monoalcohol, and polyethylene monocarboxylic acid.

In the case of a vinyl polymer, (meth) acrylic polymer or the like, reactive groups can be introduced into the polymer by copolymerizing a monomer, which contains the same reactive group(s), upon production of the polymer or by conducting post treatment after polymerization. For example, hydroxyl groups can be introduced by saponification of a copolymer containing vinyl acetate, as residual hydroxyl groups of a partial butyral derivative of polyvinyl alcohol, or by copolymerizing allyl alcohol, 2-hydroxyethyl (meth)acrylate, hydroxypropyl (meth)acrylate or the like with another monomer. Carboxyl groups can be introduced by reacting an unsaturated carboxylic acid, such as acrylic acid, methacrylic acid, itaconic acid or maleic acid, with another monomer. Acid halide groups, acid anhydride groups or lower ($C_1$–$C_3$) alkyl ester groups can be introduced by copolymerizing a corresponding derivative of an unsaturated carboxylic acid with another monomer. Epoxy groups or cholorohydrin groups can be introduced by copolymerizing glycidyl (meth)acrylate or γ-chloro-β-hydroxypropyl (meth)acrylate with another monomer. Amino groups can be introduced by saponifying a copolymer of N-vinylacetamide. Chlorotriazine groups can be introduced by reacting chlorotriazine with a polymer. Isocyanate groups can be introduced by copolymerizing methacryloyloxyethyl isocyanate or propenylphenyl isocyanate with another monomer.

Concerning a condensation polymerization or polyaddition polymer such as a polyester, polyamide, polyurethane or polyurea, reactive groups can be introduced into the polymer by adjusting the proportions of monomeric starting materials, which contain reactive groups, upon synthesis such that one of the starting materials is used somewhat excessively, by reacting a reactive compound with the polymer after reaction, or by using as a portion of a starting material a polyfunctional compound having a different reaction velocity such as trimellitic anhydride, pyromellitic anhydride, trimellitic anhydride monochloride or tolylene diisocyanate.

Owing to the use of such a reaction as described above, the functional agent and the polymer in the polymer-bonded functional agent are bonded through covalent bonds such as ester bonds, amide bonds, urethane bonds, urea bonds or ether bonds. The content of moieties of the functional agent in the molecule of the polymer-bonded functional agent may widely vary but, when the polymer-bonded functional agent is used as an additive, the moieties of the functional agent may account preferably for about 5 to 95 wt. %, notably for 20 to 80 wt. % of the polymer-bonded functional agent because the polymer-bonded functional agent has polymer properties and may be added in a small amount to a resin as a material to which the polymer-bonded functional agent is to be added. When the polymer-bonded functional agent is used as is by simply processing it, the preferred content of the moieties of the functional agent in the polymer-bonded functional agent may range from about 0.05 to about 5 wt. %.

Depending upon the number of reactive groups contained in the polymer, the amount of the functional agent to be bonded to the polymer can be adjusted. When used, for example, in or on a resin, fibers, paper, a non-woven fabric, an electrophotographic developer or an ink-jet ink, the polymer-bonded functional agent can be obtained with an appropriate content of the functional agent by determining the proportion of reactive groups in the polymer in accordance with the amount of the functional agent desired to be included in such a material. When employed, for example, in a paint, a coating formulation, a textile printing ink, a printing ink or an adhesive, it may be desired in some instances to have the added polymer-bonded functional agent crosslinked or cured so that physical properties of such a material are improved further. In this case, the polymer may be provided with more reactive groups than the functional agent so that reactive groups may remain in the polymer-bonded functional agent. The number of reactive groups, which are allowed to remain, may be substantially equivalent to the content of reactive groups in an ordinary crosslink-forming polymer. In the case of carboxyl groups, for example, the number of carboxyl groups which may be allowed to remain can be set to give an acid value of from about 1 to about 50. In the case of hydroxyl groups, on the other hand, the number of hydroxyl groups which may be allowed to remain can be set to give a hydroxyl value of from bout 1 to about 50. Further, a radiation-curable polymer-bonded functional agent can also be obtained by limiting the reaction of the functional agent below about 50% to about 80% of the reactive groups contained in the polymer and further reacting the remaining reactive groups with other reactive groups, for example, (meth)acrylic acid chloride, maleic anhydride or the like. Further, to impart solubility or dispersibility in a mixed solvent of an organic solvent and water, carboxyl groups may be allowed to remain in the polymer-bonded functional agent. When carboxyl groups are introduced as an alternative, the acid value may be set at about 10 to about 200.

Conditions under which the polymer-bonded functional agent is produced, that is, conditions under which a reaction is conducted between at least one functional agent containing reactive groups and a polymer containing groups reactive with the first-mentioned reactive groups may be similar to reaction conditions for general condensation or addition reactions. A description will be made taking as an example an esterification reaction between ethylene-vinyl alcohol copolymer and a carboxyl-containing functional agent. Examples of a reaction solvent can include aromatic hydrocarbons such as toluene, xylene and ethylbenzene; and chlorinated hydrocarbons such as monochlorobenzene, dichlorobenzene and 1-chloronaphthalene. Two or more of these organic solvents may be used as a mixed solvent.

Illustrative of a catalyst usable in the condensation or addition reaction are concentrated sulfuric acid, o-toluenesulfonic acid, m-toluenesulfonic acid, p-toluenesulfonic acid, 4-ethylbenzneusulfonic acid and 4-dimethyl-aminopyridine. The catalyst can be used in a proportion of from 0.1 to 10 parts by weight, preferably from 0.5 to 5 parts by weight per 100 parts by weight of the raw materials. The reaction temperature may generally be in a range of from 80° C. to the boiling point of the reaction solvent. To drive out reaction byproducts such as water from the reaction system, it is preferred to proceed with the reaction at 100° C. at the boiling point of the solvent. The reaction temperature may range generally from 2 to 10 hours, preferably from 4 to 6 hours although it varies depending upon the reaction temperature. It is desired to eliminate especially any unreacted portion of the functional agent by purification after completion of the reaction.

Resins, fibers, paper, non-woven fabrics, paints, coating formulations, textile printing inks, printing inks, electrophotographic developers, ink-jet inks, adhesives, cosmetics or the like can be provided with improved oxidation resistance, light stability, ultraviolet absorbability, infrared absorbability or antistatic property, when they are added with the polymer-bonded functional agent according to the present invention and are then subjected or used, for example, to or in forming, molding, spinning, paper making, film formation, coating, textile printing, printing, electrophotographic recording, ink-jet printing or bonding. It is therefore possible to solve problems such as thermal deterioration during molding, forming or processing of resins; oxidative deterioration during long-term storage or long-term use of molded or otherwise formed products; or reductions in elasticity and tensile strength, reductions in the physical properties of the resins such as occurrence of cracks, deteriorations in electrical properties, coloring, or discoloration, fading or the like of a colorant such as a pigment or dye, due to embrittlement or the like caused by sunlight, especially ultraviolet rays or the like. Other problems, which have existed as defects of conventional low molecular functional agents, can also be solved, including a reduction in the function of a functional agent due to evaporation, volatilization, sublimation or the like, a limitation to an amount of a functional agent, which can be added to a resin, due to its limited compatibility with the resin, a decrease in an effective amount of a functional agent added to a molded or otherwise formed product or a coating due to its bleeding onto a surface of the molded or otherwise formed product or a surface of the coating, and staining of other product(s) or article(s) or an impairment in printability by a bled-out functional agent. In addition, when the polymer-bonded functional agent is added to a cosmetic, human skin can be protected by applying makeup to the human skin with the thus-prepared functional cosmetic.

Examples of thermoplastic resins (plastics) to which the polymer-bonded functional agent according to the present invention can be added can include resins such as polyethylene, polypropylene, poly(meth)acrylate esters, polystyrene, styrene-acrylonitrile copolymer, acrylonitrile-butadiene-styrene copolymer, polyvinyl chloride, polyvinylidene chloride, polyvinyl acetate, polyvinylbutyral, ethylene-vinyl acetate copolymer, ethylene-vinyl alcohol copolymer, polyethylene terephthalate (PET), polybutylene terephthalate (PBT), liquid crystal polyesters (LCPs), polyacetals (e.g., POM), polyamides (PA), polycarbonates, polyurethane and polyphenylene sulfide (PPS); polymer blends or polymer alloys formed of two or more of these resins; and compounds obtained by adding fillers such as glass fibers, carbon fibers, semi-carbonized fibers, cellulose fibers and glass beads, flame retardants, blowing agents, antimicrobial agents, crosslinking agents, fine polyolefin resin powder, polyolefin waxes, ethylene bisamide waxes, metallic soaps and the like either singly or in combination to these resins. Examples of thermosetting resins, on the other hand, can include thermosetting resins such as epoxy resins, melamine resins and unsaturated polyester resins; and compounds obtained by incorporating fillers such as glass fibers, carbon fibers, semi-carbonized fibers, cellulose fibers and glass beads, flame retardants and the like either singly or in combination to these resins.

The polymer-bonded functional agent according to the present invention can be added in a desired amount to the above-described resin. To 100 parts by weight of the resin, the polymer-bonded functional agent may be added in a proportion of from about 0.05 to about 20 parts by weight, preferably from about 0.1 to about 10 part by weight as calculated in terms of the amount of the functional agent component in the polymer-bonded functional agent. Depending upon the application purpose or kind of the resin added with such polymer-bonded functional agent, polymer-bonded ultraviolet absorbers, polymer-bonded light stabilizers, polymer-bonded antioxidants, polymer-bonded antistatic agents and the like can be used either singly or in combination.

To add the polymer-bonded functional agent according to the present invention to the resin, the polymer-bonded functional agent and the resin are compounded in predetermined proportions, and by a mixing roll, Banbury mixer or kneader, the resulting compound is kneaded into granules of an appropriate size for use in molding or forming. To add the polymer-bonded functional agent at a high concentration, the kneaded compound is blended as a master batch with the resin in predetermined proportions, and the resulting resin blend is molded or otherwise formed into various articles or products. Illustrative molding or forming processes can include injection molding, extrusion, and inflation molding.

Examples of fibers to which the polymer-bonded functional agent according to the present invention is applicable can include fibers of polyethylene terephthalate, polyamides, polypropylene, acrylonitrile, polyurethane, polyethylene, polyvinyl chloride, polyvinylidene chloride and the like. The polymer-bonded functional agent can be added to fibers in a proportion of from about 0.1 to about 5 parts by weight per 100 parts by weight of fibers as calculated in terms of the functional agent component.

The polymer-bonded functional agent according to the present invention can be applied to paper, non-woven fabrics, paints, coating formulations, textile printing inks, printing inks and adhesives. Illustrative of the paints are oil-based paints such as acrylic melamine paints, alkyd melamine paints, polyester melamine paints, acrylic isocyanate paints and two-pack polyurethane paints; water-based paints such as acrylic melamine paints and alkyd melamine paints; aqueous dispersions such as acrylic resin emulsions and fluorinated resin emulsions; powder coating formulations such as acrylic isocyanate powder coating formulations, polyester isocyanate powder coating formulations and polyester acrylate powder coating formulations; ultraviolet curing or electron beam curing coating formulations such as urethane acrylate coating formulations, epoxy acrylate coating formulations and polyester acrylate coating formulations. These paints or coating formulations can be applied to metal plates, especially metal plates for automotive vehicles, coils of zinc coated steel, construction or building materials, wood working materials, and the like. Incidentally, examples of coating formulations or adhesives to which the polymer-bonded functional agent according to the present invention is applicable can also include those of both dry and wet types.

Examples of textile printing inks to which the polymer-bonded functional agent according to the present invention is applicable can include those of the acrylic resin emulsion type, acrylstyrene resin emulsion type and synthetic rubber type. Illustrative of printing inks to which the polymer-bonded functional agent according to the present invention is applicable are offset inks such as rotary letterpress inks and sheet-feed press inks; gravure inks for resin films or sheets, aluminum foils, construction or building materials, and decorative laminates; and inks for metal plates. Illustrative of electrophotographic developers or ink-jet inks to which the polymer-bonded functional agent according to the present invention is applicable are full-color, mono-color or monochrome, dry developers, wet developers, and water-based, oil-based or solid-type ink-jet inks. The polymer-bonded functional agent is effective especially when it is used in developers or inks for full-color pictures on billboards, signboards or the like.

The amount of the polymer-bonded functional agent to be added to each of the above-mentioned materials varies depending upon the kind of the polymer-bonded functional agent and the application purpose of the material, but as a standard, the polymer-bonded functional agent may be used, per 100 parts by weight of resin solid, in a proportion of from about 0.1 to 10 parts by weight as calculated in terms of the functional agent component. In these application fields, two or more polymer-bonded functional agents can also be used in combination.

When a product is thin like a film or is fine like threads, when a material is susceptible to deterioration, or when a product is supposed to retain durability over long time despite its use condition that it is exposed to a severe environment like an exterior paint, it is generally desired to use the polymer-bonded functional agent according to the present invention in a greater proportion within the above-described range.

As a wet processing method for treating the above-described materials with the polymer-bonded functional agent according to the present invention, mixing in a reaction tank equipped with heating and stirring means, mixing in a reaction tank equipped with mixing an stirring means, mixing in a dissolver can be mentioned. For processing by wet dispersion, it is possible to use a mixing roll mill, a kneader, a ball mill, an attritor, a sand mill, a medium-containing horizontal disperser, a medium-containing upright disperser, a continuous medium-containing horizontal disperser, a continuous medium-containing upright disperser or the like. For dry dissolution or dispersion processing, the methods and processing machines described above in connection with resins can be used.

Examples of dyes usable upon coloring the above-described resins or products such as paints, textile printing inks, printing inks, electrophotographic developers or ink-jet inks can include organic pigments, inorganic pigments, extender pigments and dyes, all of which are commonly used.

As a method for applying the polymer-bonded functional agent according to the present invention to improve the durability of a pigment against discoloration, fading or the like, the polymer-bonded functional agent can be added upon preparation of a resin colorant composition, a paint, a textile printing ink, a printing ink, an electrophotographic developer, an ink-jet ink or the like, or the pigment may be produced by adding the polymer-bonded functional agent beforehand in the course of the production of the pigment.

Among polymer-bonded functional agents according to the present invention, polymer-bonded ultraviolet absorbers can each be obtained by subjecting an ultraviolet absorber— for example, a benzoic acid ultraviolet absorber such as benzoic acid, p-aminobenzoic acid or p-dimethylaminobenzoic acid, a cinnamic acid ultraviolet absorber such as cinnamic acid or p-methoxycinnamic acid, salicylic acid or the like, or an acid chloride compound thereof—to a condensation or addition reaction with the above-described reactive polymer. These polymer-blended ultraviolet absorbers can be used, for example, in sunburn-preventing products as medicated cosmetics. As these polymer-blended ultraviolet absorbers have high safety to skin and effectively absorb UV-A (320–400 nm) and UV-B (290–320 nm) which are harmful to skin, the polymer-blended ultraviolet absorbers are added to cosmetic bases such creams, milky lotions, oils and lotions. The amount of each polymer-blended ultraviolet absorber to be added varies depending upon the exposed condition of skin, the application purpose, the used material and the like and cannot be set in a wholesale manner, but the polymer-blended ultraviolet absorber may account for about 1 to 20 wt. % of each product as calculated in terms of the ultraviolet absorber.

The present invention will hereinafter be described more specifically based on Synthesis Examples and Examples. It is however to be noted that the present invention is by no means limited by these Examples. In the following Examples, the designations of "part", "parts" and "%" are by weight basis.

SYNTHESIS EXAMPLE 1
(Synthesis of Polymer-Bonded Antioxidant No. 1)

Charged into a reaction vessel fitted with a thermometer, a stirrer, a water-quantitating receptacle and a reflux condenser were 40.0 parts of an ethylene-vinyl alcohol copolymer (hereinafter abbreviated as "EVAOH") (weight ratio: 83.2/16.8, hydroxyl equivalent: 266.1), 200 parts of xylene and 46.0 parts of 3-(3',5'-di-t-butyl-4'-hydroxyphenyl) propionic acid. Under heat, the contents were converted into a solution. As a catalyst, 0.3 part of p-toluenesulfonic acid was added, followed by a reaction at 140° C. under heat. Water produced during the reaction was taken out of the reaction system by the water-quantitating receptacle. The esterification reaction was allowed to proceed while checking the progress of the reaction by infrared spectroscopy.

After completion of the reaction, the reaction mixture was cooled and then poured into isopropyl alcohol (IPA) to precipitate the reaction product. The precipitate was collected by filtration, washed with IPA and then dried, whereby 71.8 parts of Polymer-bonded antioxidant No. 1 were obtained. The product was confirmed based on an infrared absorption spectrum and NMR data. Its number average molecular weight and weight average molecular weight as determined by GPC (gel permeation chromatography) were about 55,000 and about 290,000, respectively.

Thermal stability tests of Polymer-bonded antioxidant No. 1 obtained as described above were conducted by thermal analyses to compare it with known antioxidants, 2,6-di-t-butyl-p-cresol (BHT, hereinafter called "Known antioxidant No. 1") and pentaerythritol-tetrakis[3-(3',5'-di-t-butyl-4'-hydroxyphenyl)-propionate] (hereinafter called "Known antioxidant No. 2"). The decomposition initiating temperature was measured by differential thermal analysis (DTA), and the weight loss was measured by thermogravimetry. The thermal analysis was conducted under an air stream at a heating rate of 10° C./min. The contents of moieties of the respective antioxidants were calculated in terms of 2,6-di-t-butyl phenyl (hereinafter called "BP") moieties, and are presented in Table 1. The results of the thermal stability tests are also presented in Table 1.

TABLE 1

Results of Thermal Stability Tests

|  | Polymer-bonded antioxidant No. 1 | Known antioxidant No. 1 | Known antioxidant No. 2 |
| --- | --- | --- | --- |
| Content in terms of BP moieties | 38% | 94% | 70% |
| Decomposition initiating temperature | 317° C. | 193° C. | 312° C. |
| Percentage of weight loss | | | |
| 100° C. | 1.1% | 1.1% | 0.2% |
| 200° C. | 2.4% | 86.1% | 0.4% |
| 300° C. | 5.6% | 89.6% | 2.6% |

The decomposition initiating temperature of Polymer-bonded antioxidant No. 1 is as high as 317° C. Although a small weight loss is observed, this weight loss is believed to be attributable to the polymer component. Like Known antioxidant No. 2, Polymer-bonded antioxidant No. 1 is therefore usable practically up to 300° C. Known antioxidant No. 1, however, underwent a sudden substantial weight loss due to sublimation at 193° C. so that a limitation is imposed on its use conditions.

SYNTHESIS EXAMPLES 2–4
(Synthesis of Polymer-Bonded Antioxidants Nos. 2–4)

Polymer-bonded antioxidants Nos. 2–4 were synthesized in a similar manner as in Synthesis Example 1 except that the ethylene-vinyl alcohol copolymers shown in Table 2 were used, respectively, in place of the EVAOH employed in Synthesis Example 1. The contents of moieties of the antioxidant in the respective polymer-bonded antioxidants were calculated in terms of BP moieties, and are presented in Table 2.

TABLE 2

Ethylene-Vinyl Alcohol Copolymers and Polymer-bonded Antioxidants

| | Ethylene-vinyl alcohol copolymer | | Polymer-bonded antioxidant | | |
|---|---|---|---|---|---|
| Synthesis example | Polymer name | Amount (parts) | Anti- oxidant No. | Content in terms of BP moieties | Average molecular weight |
| 2 | Ethylene-vinyl alcohol-vinyl acetate copolymer (weight ratio: 82.1/14.7/3.1, hydroxyl equivalent: 299.6) | 45.0 | No. 2 | 36% | Number average: 50,000 Weight average: 270,000 |
| 3 | EVAOH (weight ratio: 79.9/20.1, hydroxyl equivalent: 218.9) | 32.9 | No. 3 | 42% | Number average: 60,000 Weight average: 330,000 |
| 4 | EVAOH (weight ratio: 92.3/7.7, hydroxyl equivalent: 573.0) | 86.1 | No. 4 | 24% | Number average: 40,000 Weight average: 220,000 |

SYNTHESIS EXAMPLES 5–6
(Synthesis of Polymer-Bonded Antioxidants Nos. 5–6)

Polymer-bonded antioxidants Nos. 5–6 were synthesized in a similar manner as in Synthesis Example 1 except that the carboxyl-containing antioxidants shown in Table 3 were used, respectively, in place of 3-(3',5'-di-t-butyl-4'-hydroxyphenyl)propionic acid. The content of moieties of the antioxidant in each polymer-bonded antioxidant was calculated in terms of BP moieties, and is presented in Table 3.

TABLE 3

Carboxyl-containing Antioxidants and Polymer-bonded Antioxidants

| | Carboxyl-containing antioxidant | | Polymer-bonded antioxidant | |
|---|---|---|---|---|
| Synthesis example | Compound name | Amount (part) | No. | Content in terms of BP moieties |
| 5 | 3-(3'-t-Butyl-5'-methyl-4'-hydroxyphenyl)-propionic acid | 39.0 | No. 5 | 41% |
| 6 | 3,5-di-5-Butyl-4-hydroxybenzoic acid | 41.3 | No. 6 | 40% |

SYNTHESIS EXAMPLE 7
(Synthesis of Polymer-Bonded Ultraviolet Absorber No. 1)

3-[3'-(2"H-Benzotriazol-2"-yl)-4'-hydroxyphenyl)]-propionic acid was reacted beforehand with thionyl chloride in a chlorine-containing solvent by a method known per se in the art, whereby it was converted into its acid chloride. Charged next into a reaction vessel fitted with a thermometer, a stirrer and a reflux condenser equipped with a desiccant-packed trap were 40.0 parts of an ethylene-vinyl alcohol copolymer of the same kind as that employed in Synthesis Example 2,500 parts of toluene and 59.0 parts of 3-[3'-(2"H-benzotriazol-2"-yl)-4'-hydroxyphenyl)]propionic acid chloride obtained in the above. The contents were converted into a solution under heat, followed by heating under reflux for 5 hours and a half. After the reaction mixture was allowed to cool down, 200 parts of water were added. The resulting mixture was neutralized with sodium carbonate, and the mixture so obtained was poured into IPA, whereby the reaction product was caused to precipitate. The precipitate was collected by filtration, washed thoroughly with water and IPA and then dried, whereby 82.3 parts of Polymer-bonded ultraviolet absorber No. 1 were obtained.

The product was confirmed based on an infrared absorption spectrum and NMR data. Its number average molecular weight and weight average molecular weight as determined by GPC were about 37,000 and about 150,000, respectively. The content of moieties of the ultraviolet absorber was found to be 34% as calculated in terms of 2-(2"-benzotriazol-2"-yl)-phenol (hereinafter called "BTA") moieties. Further, an ultraviolet-visible absorption spectrum of a solution obtained by dissolving the product at a concentration of 100 mg/L in dichloromethane was measured using a quartz cell. Significant absorptions were observed at 304 nm and 344 nm, respectively.

SYNTHESIS EXAMPLE 8
(Synthesis of Polymer-Bonded Ultraviolet Absorber No. 2)

78.6 Parts of a xylene solution with 28.6 parts of 2-[4"-[(2"'-chlorocarbonyl-propionyloxy)-3"'-dodecyloxy-propyloxy]-2"-hydroxyphenyl]-4,6-bis(2',4'-dimethylphenyl)-1,3,5-triazine dissolved therein were prepared beforehand. In a reaction vessel fitted with a thermometer, a stirrer and a reflux condenser, 40 parts of an ethylene-vinyl alcohol copolymer of the same kind as that employed in Synthesis Example 2 was added to 500 parts of xylene, and the copolymer was dissolved in the xylene. 44.4 Parts of 3-[3'-(2"H-benzotriazol-2"-yl)-4'-hydroxyphenyl)] propionic acid chloride obtained in Synthesis Example 7 were then charged into the reaction vessel, followed by dissolution under heat. The resulting mixture was stirred at 120° C. for 2 hours under stirring. The xylene solution of the carboxylic acid chloride of the azine ultraviolet absorber, which had been prepared in the above, was then added, followed by a reaction at 130° C. for 2 hours. After the reaction mixture was allowed to cool down, 200 parts of IPA and 200 parts of water were added, followed by neutralization with sodium carbonate. The thus-obtained mixture was poured into IPA, whereby the reaction product was caused to precipitate. The precipitate was collected by filtration, washed thoroughly with water and IPA, and then dried, whereby 93.9 parts of Polymer-bonded ultraviolet absorber No. 2 were obtained.

The product was confirmed based on an infrared absorption spectrum and NMR data. The content of moieties of the ultraviolet absorber was found to be 22% as calculated in terms of BTA moieties and also to be 12% in terms of 2-(2'-hydroxy-phenyl)-4,6-bis(phenyl)-1,3,5-triazine (hereinafter called "TAZ") moieties, and accordingly, the total content as calculated in terms of both moieties was 34%. Polymer-bonded ultraviolet absorber No. 2 was dissolved in dichloromethane in a similar manner as in Synthesis Example 7, and its ultraviolet-visible absorption spectrum was measured. Significant absorptions were observed at 299 nm and 342 nm, respectively.

SYNTHESIS EXAMPLE 9
(Synthesis of Polymer-Bonded Ultraviolet Absorber No. 3)

A reaction was conducted in a similar manner as in Synthesis Example 8 except that the charged amount of 3-[3'-(2"H-benzotriazol-2"-yl)-4'-hydroxyphenyl)]propionic acid chloride was changed to 26.9 parts. The content of moieties of the ultraviolet absorber in Polymer-bonded ultraviolet absorber No. 3 so obtained was found to be 17% as calculated in terms of BTA moieties and also to be 13% in terms of TAZ moieties, and accordingly, the total content as calculated in terms of both moieties was 30%. In an ultraviolet-visible absorption spectrum, significant absorptions were observed at 299 nm and 342 nm, respectively. A hydroxyl value based on remaining hydroxyl groups was about 26.

SYNTHESIS EXAMPLE 10
(Synthesis of Polymer-Bonded Light Stabilizer No. 1)

In a reaction vessel fitted with a thermometer, a stirrer and a reflux condenser, 70.7 parts of an ethylene-acrylic acid copolymer (weight ratio: 74.5/25.5, carboxyl equivalent: 282.6) were dissolved in 500 parts of monochlorobenzene, and by using thionyl chloride, the copolymer was converted into an acid chloride in a manner known per se in the art. 46.7 Parts of 4-hydroxy-1,2,2,6,6-pentamethylpiperidine were then charged. The resulting mixture was heated for 5 hours under reflux to react the contents. After the reaction mixture was allowed to cool down, 200 parts of water were added, followed by neutralization with sodium carbonate. The mixture so obtained was poured into IPA to precipitate the reaction product. The precipitate was collected by filtration, washed thoroughly with water and IPA, and then dried, whereby 98.7 parts of Polymer-bonded light stabilizer No. 1 were obtained. The product was confirmed based on an infrared absorption spectrum and NMR data. The content of moieties of the light stabilizer in Polymer-bonded light stabilizer No. 1 so obtained was found to be 31% as calculated in terms of 2,2,6,6-tetramethylpiperidine (hereinafter called "TMP") moieties.

SYNTHESIS EXAMPLE 11
(Synthesis of Polymer-Bonded Light Stabilizer No. 2)

A reaction was conducted in a similar manner as in Synthesis Example 10 except that the amount of charged 4-hydroxy-1,2,2,6,6-pentamethylpiperidine was changed to 33.9 parts, whereby 91.9 parts of Polymer-bonded light stabilizer No. 2 were obtained. The content of moieties of the light stabilizer in Polymer-bonded light stabilizer No. 2 so obtained was found to be 27% as calculated in terms of TMP moieties, and an acid value based on remaining carboxyl groups was about 34.

SYNTHESIS EXAMPLES 12–13
(Synthesis of Polymer-Bonded Light Stabilizers Nos. 3–4)

Polymer-bonded light stabilizers Nos. 3–4 were synthesized in a similar manner as in Synthesis Example 10 except that the hydroxyl-containing light stabilizers shown in Table 4 were used, respectively, in place of 4-hydroxy-1,2,2,6,6-pentamethylpyridine. The contents of moieties of the light stabilizers as calculated in terms of TMP moieties are presented in Table 4.

TABLE 4

Hydroxyl-containing Light Stabilizers and Polymer-bonded Light Stabilizers

| | Hydroxyl-containing light stabilizer | | Polymer-bonded light stabilizer | |
|---|---|---|---|---|
| Synthesis example | Compound name | Amount (part) | No. | Content in terms of TMP moieties |
| 12 | 4-Hydroxy-2,2,6,6-tetramethyl-piperidine | 42.9 | No. 3 | 32% |
| 13 | 1-Octyloxy-4-hydroxy-2,2,6,6-tetramethyl-piperidine | 77.8 | No. 4 | 25% |

SYNTHESIS EXAMPLE 14
(Synthesis of Polymer-Bonded Antistatic Agent No. 1)

In a reaction vessel fitted with a thermometer, a stirrer and a reflux condenser, 72.0 parts of an ethylene-acrylic acid copolymer (weight ratio: 90.0/10.0, carboxyl equivalent: 720.5) were dissolved in 250 parts of monochlorobenzene, and by using thionyl chloride, the copolymer was converted into an acid chloride in a manner known per se in the art. 92.2 Parts of an ethylene glycol-propylene glycol copolymer monobutyl ether (weight ratio: 50/50, number average molecular weight: about 970) and 250 parts of methyl isobutyl ketone were then charged. The resulting mixture was heated under reflux. An esterification reaction was allowed to proceed for 5 hours while checking the progress of the reaction by infrared absorption spectroscopy. After completion of the reaction, the reaction mixture was allowed to cool down. 200 Parts of water were added, followed by neutralization with sodium carbonate. The mixture so obtained was poured into propyl alcohol to precipitate the reaction product. The precipitate was collected by filtration, washed thoroughly with water and IPA, and then dried, whereby 151 parts of Polymer-bonded antistatic agent No. 1 were obtained. The product was confirmed based on an infrared absorption spectrum and NMR data. The content of moieties of the ethylene glycol-propylene glycol copolymer (hereinafter called "PEP") was found to be 55%.

SYNTHESIS EXAMPLE 15
(Synthesis of Polymer-Bonded Antistatic Agent No. 2)

Using thionyl chloride, 70.0 parts of an ethylene-acrylic acid copolymer (weight ratio: 74.5/25.5, carboxyl equivalent: 282.6) were converted into an acid chloride in a similar manner as in Synthesis Example 14. 46.7 Parts of diethylaminoethanol were then charged and reacted. After the reaction, neutralization, filtration, washing and drying were conducted, whereby 98.7 parts of Polymer-bonded antistatic agent No. 2 were obtained. The product was confirmed based on an infrared absorption spectrum and NMR data. The content of diethylaminoethylene (hereinafter called "DEA") moieties was found to be 22%.

EXAMPLE 1
(Production of Pellets of Polymer-Bonded Functional Agents)

Through a mixing roll (roll surface temperature: 50° C.), Polymer-bonded antioxidant No. 1 obtained in Synthesis Example 1 was kneaded and formed into a sheet. The sheet was then formed by a pelletizer into polymer-bonded antioxidant pellets of about 3×3×2 mm, which contained moieties of the antioxidant at a concentration of 36% as calculated in terms of BP moieties.

Likewise, Polymer-bonded antioxidants Nos. 2–6, Polymer-bonded ultraviolet absorbers Nos. 1–3, Polymer-bonded light stabilizers Nos. 1–4 and Polymer-bonded antistatic agents Nos. 1–2, which had been obtained in Synthesis Examples 2–15, were formed into pellets or sheets.

EXAMPLE 2
(Production of Master Batches Containing Polymer-Bonded Antioxidants)

Through a mixing roll (roll surface temperature: 120° C.), 55.6 parts of Polymer-bonded antioxidant No. 1 obtained in Synthesis Example 1 were kneaded with 44.4 parts of low-density polyethylene (specific gravity: 0.918, MFR: 12), and a sheet was formed. A master batch containing the polymer-bonded antioxidant was then obtained in the form of pellets of about 3×3×2 mm by a pelletizer. The master batch was found to contain moieties of the antioxidant at a concentration of 20% as calculated in terms of BP moieties.

Likewise, Polymer-bonded antioxidants Nos. 2–6, Polymer-bonded ultraviolet absorbers Nos. 1–3, Polymer-bonded light stabilizers Nos. 1–4 and Polymer-bonded antistatic agents Nos. 1–2, which had been obtained in Synthesis Examples 2–15, were kneaded with the polyethylene, and sheets were formed. Those sheets were either shred or processed by a pelletizer, whereby they were formulated into master batches with their corresponding functional agents contained at a converted concentration of 20%.

EXAMPLE 3
(Production of Master Batches Containing Polymer-Bonded Antioxidants)

In a high-speed mixer (Henschel mixer), 86.1 parts of low-density polyethylene (specific gravity: 0.918, MFR: 12) and 13.9 parts of Polymer-bonded antioxidant No. 1 obtained in Synthesis Example 1 were thoroughly mixed. Through a twin-screw extruder, the resulting compound was kneaded and pelletized at 130 to 150° C., whereby a master batch containing the polymer-bonded antioxidant was obtained in the form of cylindrical pellets of about 3×3 mm. The master batch contained moieties of the antioxidant at a concentration of 5% as calculated in terms of BP moieties.

Likewise, Polymer-bonded antioxidants Nos. 2–6, Polymer-bonded ultraviolet absorbers Nos. 1–3, Polymer-bonded light stabilizers Nos. 1–4 and Polymer-bonded antistatic agents Nos. 1–2, which had been obtained in Synthesis Examples 2–15, were kneaded with the polyethylene, and the resulting compounds were pelletized. They were hence formulated into master batches with their corresponding functional agents contained at a converted concentration of 5%.

EXAMPLE 4

Through a mixing roll (roll surface temperature: 120° C.), the polyethylene master batch of Polymer-bonded antioxidant No. 1 obtained in Example 2 (content of moieties of the antioxidant: 20% as calculated in terms of BP moieties) was added at 0.25% and 1.0% (0.05% and 0.2% as calculated in terms of BP moieties), respectively, to low-density polyethylene (specific gravity: 0.918, MFR: 12), and the resulting compounds were separately kneaded and formed into sheets. For the sake of comparison, Known antioxidants Nos. 1 and 2 were similarly added such that their contents became 0.05% and 0.2% as calculated in terms of BP moieties, and the resulting compounds were likewise separately kneaded and formed into sheets. To determine the thermal stability of the thus-obtained low-density polyethylene sheets with Polymer-bonded antioxidant No. 1 contained therein, said thermal stability being useful as indices of their oxidation-preventing ability, their oxidation initiating temperatures were measured by differential thermal analysis (DTA). The sheets—which contained Known antioxidants Nos. 1 and 2, respectively—were also measured likewise. The results of the measurements are shown in the first section in Table 5. DTA was measured at a heating rate of 10° C./min under an air stream. According to the oxidation initiating temperatures measured by DTA, improvements were observed on all the sheets over a corresponding sheet obtained without addition of any antioxidant.

Further, improvements were also observed on all sheets—which were produced using the master batches with Polymer-bonded antioxidants Nos. 2 to 6, respectively—over the corresponding sheet obtained without addition of any antioxidant.

EXAMPLE 5

In a similar manner as in Example 4, a low-density polyethylene sheet was produced with Polymer-bonded antioxidant No. 1 added at 2% (content calculated in terms of BP moieties: 0.4%). The thus-obtained film was heated at 50° C. in a Geer oven. Based on percent changes in characteristic absorption by infrared spectroscopy, the antioxidant component was compared in thermal stability with Known antioxidants Nos. 1 and 2 contained in sheets treated likewise. The results are shown in the second section in Table 5. By a comparison of their amounts remaining along the passage of time during the heating as determined by infrared spectroscopy, Polymer-bonded antioxidant No. 1 was not observed to undergo any changes and its content remained unchanged, while Known antioxidant No. 1 was not found to remain due to sublimation and Known antioxidant No. 2 was also found to be lost by about 20% five days later.

Further, no changes were observed on sheets produced by using master batches—which contained Polymer-bonded antioxidants Nos. 2 to 6, respectively—and no decreases by vaporization or the like were observed on the contents of the respective antioxidants.

EXAMPLE 6

With 94.7 parts of low-density polyethylene, 3.3 parts of a master batch of carbon black pigment (pigment content: 30%) and 2 parts (content of moieties of the antioxidant: 0.4 part as calculated in terms of BP moieties) of the polyethylene master batch (content of moieties of the antioxidant: 20% as calculated in terms of BP moieties) of Polymer-bonded antioxidant No. 1, said polyethylene master batch having had been obtained in Example 2, were mixed. The resulting compound was kneaded for 2 minutes through a mixing roll (roll surface temperature: 120° C.) and then formed by a hot press (160° C., 100 kg/cm$^2$, 1 minute), whereby a black film of about 0.15 mm was obtained. Likewise, using Known antioxidants No. 1 and 2, they were separately added to portions of the low-density polyethylene such that their contents became 0.4% as calculated in terms of BP moieties, and the thus-obtained compounds were kneaded and formed, whereby black films of about 0.15 mm were obtained, respectively.

The thus-obtained film was heated at 60° C. in a Geer oven, and bleeding of the antioxidant onto a surface of the polyethylene sheet was investigated based on the extent of surface fogging. The extent of that surface fogging was compared with those of the sheets which contained Known antioxidants Nos. 1 and 2, respectively. In the bleeding test, the polyethylene sheet making use of Polymer-bonded antioxidant No. 1 did not show any bleeding onto the surface. The polyethylene sheet which used Known antioxidant No. 2, on the other hand, developed substantial bleeding of the antioxidant onto the surface. Further, the sheet obtained using Known antioxidant No. 1 remained unchanged on the surface thereof. This, however, is attributed to sublimation of the antioxidant at 60° C. and hence to no antioxidant remaining in the sheet.

Sheets—which were likewise obtained by using the master batches of Polymer-bonded antioxidants Nos. 2 to 6, respectively—also showed absolutely no bleeding onto surfaces.

TABLE 5

Results of Thermal Stability Test on Polyethylene Sheets

|  | Polymer-bonded antioxidant No. 1 | Known antioxidant No. 1 | Known antioxidant No. 2 |
|---|---|---|---|
| Improvements in thermal decomposition temperature (DTA oxidation initiating temperature) |  |  |  |
| Not added Content in terms of BP moieties | 220° C. | 220° C. | 220° C. |
| 0.05% addition | 226° C. | 221° C. | 239° C. |
| 0.2% addition | 233° C. | 225° C. | 256° C. |
| Remaining ability along the passage of time during heating (Relative comparison by infrared spectroscopy) |  |  |  |
| Before heat treatment | 100 | 100 | 100 |
| 50° C., 1 day | 100 | 0 | 99 |
| 50° C., 5 days | 100 | 0 | 81 |
| Blooming onto the surface |  |  |  |
| 60° C., 1 day | No bleeding | (No bleeding due to complete loss of antioxidant by sublimation) | Substantial bleeding |
| 60° C., 5 days | No bleeding |  | Substantial bleeding |

EXAMPLE 7

To portions of LLD (linear low density) polyethylene (specific gravity: 0.920, MFR: 2.1), the polyethylene master batch containing Polymer-bonded ultraviolet absorbent No. 1 and the polyethylene master batch containing Polymer-bonded ultraviolet absorbent No. 2, both of said master batches having had been obtained in Example 2, were added at 0.5% (content in the resin as calculated in terms of BTA moieties: 0.1%) and 0.5% (total content in the resin as calculated in terms of TAZ and BTA moieties: 0.1%), respectively, in mixers. The resulting compounds were separately processed thorough a 30-mm inflation extruder, whereby films of 50 μm in thickness were obtained, respectively. For the sake of comparison, 2-(3'-t-butyl-5'-methyl-2'-hydroxy-phenyl)-2H-5-chloro-benzotriazole (content as calculated in terms of BTA moieties: 67%, hereinafter called "Known ultraviolet absorber No. 1") and bis(2,2,6,6-tetramethyl-4-piperidyl)sebacate (content as calculated in terms of TMP moieties: 59%, hereinafter called "Known light stabilizer No. 1) were added in combination at 0.15% (content in the resin as calculated in terms of BTA moieties: 0.1%) and 0.15% (content in the resin as calculated in terms of TMP moieties: 0.09%), respectively, to the low-density polyethylene. The resulting compound was kneaded, and by the inflation extruder, a film of 50 µm in thickness was obtained.

To determine the ultraviolet deterioration resisting ability of the resultant polyethylene films containing the polymer-bonded ultraviolet absorbers, respectively, a weatherability test was conducted by an accelerated weathering tester ("Sunshine Weather-O-Meter", trade mark; 63° C., spray cycle: 12 min/hr). The degrees of ultraviolet deterioration of the films were determined based on changes in the percent elongations of the films (pulling rate: 200 mm/min), and were compared with that of the film which used Known ultraviolet absorber No. 1 and Known light stabilizer No. 1 in combination. The measurement results are shown in Table 6. A polyethylene film added with no ultraviolet absorber was observed to undergo substantial deterioration along the passage of time, whereas those added with the ultraviolet absorbers, respectively, all showed only small changes. Effects of the ultraviolet absorbers were hence observed. Especially, the films with the corresponding polymer-bonded ultraviolet absorbers contained therein underwent an extremely small decrease of approximately 10% in the percentage of retention of strength at break, thereby demonstrating that the polymer-bonded ultraviolet absorbers are excellent in the long-term persistency of ultraviolet deterioration preventing effect. The film with the known light stabilizer added further in addition to the known ultraviolet absorber was reduced by more than 20% in strength at break, resulting in inferiority to the polymer-bonded ultraviolet absorbers. As each of the added known functional agents has a low molecular weight, it is believed from additional consideration of the results of Example 8 that the known functional agents were caused to bleed or evaporate, resulting in decreases in the contents of the effective components.

Incidentally, combined use of a polymer-bonded light stabilizer and/or a polymer-bonded antioxidant with a polymer-bonded ultraviolet absorber makes it possible to provide a film with still improved physical properties.

TABLE 6

Results of Accelerated Weathering Test on Polyethylene Sheets (Compared by tensile test)

|  | Irradiation time (hr) | Strength at break | | Rate of elongation | |
| --- | --- | --- | --- | --- | --- |
|  |  | kg/mm² | Percentage of retention | Elongation, % | Percentage of retention |
| Feed polyethylene (LLDPE) alone | 0 | 3.61 | 100 | 680 | 100 |
|  | 400 | 2.06 | 57 | 650 | 96 |
|  | 600 | 1.81 | 50 | 630 | 93 |
| Polyethylene with Polymer-bonded ultraviolet absorber No. 1 | 0 | 3.23 | 100 | 660 | 100 |
|  | 400 | 2.99 | 93 | 630 | 95 |
|  | 600 | 2.91 | 90 | 680 | 103 |
| Polyethylene with Polymer-bonded ultraviolet absorber No. 2 | 0 | 3.52 | 100 | 680 | 100 |
|  | 400 | 3.23 | 92 | 690 | 101 |
|  | 600 | 3.14 | 89 | 690 | 101 |
| Polyethylene with Known ultraviolet absorber No. 1 and Known light stabilizer No. 1 | 0 | 3.47 | 100 | 700 | 100 |
|  | 400 | 3.06 | 88 | 640 | 91 |
|  | 600 | 2.74 | 78 | 650 | 93 |

EXAMPLE 8

With low-density polyethylene (specific gravity: 0.918, MFR: 12), a master batch of carbon black pigment (pigment content: 30%) and the polyethylene master batch of Polymer-bonded ultraviolet absorber No. 1, said polyethylene master batch having had been obtained in Example 2, were mixed such that the content of the former master batch became at 3.3% and that of the latter master batch became 0.68% as calculated in terms of BTA moieties. In addition, a polyethylene master batch of Polymer-bonded ultraviolet absorber No. 2 was mixed with the low density polyethylene such that the total content of the ultraviolet absorber as calculated in terms of TAZ and BTA moieties became 0.68%. The resulting compounds were separately kneaded for 2 minutes through a mixing roll (roll surface temperature: 120° C.) and then formed by a hot press (160° C., 100 kg/cm², 1 min), whereby two types of black films of about 0.15 mm in thickness were obtained with Polymer-bonded ultraviolet absorbers Nos. 1 and 2 contained therein, respectively. Likewise, Known ultraviolet absorber No. 1 was added to the low-density polyethylene such that the content of the ultraviolet absorber became 0.68% as calculated in terms of BTP moieties, and the resulting compound was kneaded and formed, whereby a black film of about 0.15 mm in thickness was obtained.

The thus-obtained films making use of the polymer-bonded ultraviolet absorbers were heated in a Geer oven controlled at 60° C., and were then examined for fogging on their surfaces to determine the degrees of bleeding of the ultraviolet absorbers onto the surfaces. The results were compared with those of the film making use of Known ultraviolet absorber No. 1, and both of the results are presented in Table 7.

As is understood from the results of the bleeding test, the polyethylene sheets—which used the polymer-bonded ultraviolet absorbers, respectively—did not develop any bleeding onto their surfaces. The film making use of Known ultraviolet absorber No. 1, on the other hand, developed substantial bleeding of the ultraviolet absorber onto its surface.

TABLE 7

Results of Test on Bleeding onto Surface of Polyethylene Sheets

|  | Polyethylene with Polymer-bonded ultraviolet absorber No. 1 | Polyethylene with Polymer-bonded ultraviolet absorber No. 2 | Polyethylene with Known ultraviolet absorber No. 1 |
|---|---|---|---|
| 60° C., 1 day | No bleeding | No bleeding | Substantial bleeding |
| 60° C., 5 days | No bleeding | No bleeding | Substantial bleeding |

EXAMPLE 9

A master batch for coloring a composite material for automotive vehicles was prepared as will be described hereinafter. 95 Parts of a propylene block copolymer, 5 parts of LLD polyethylene, 10 parts of talc, 20 parts of titanium oxide, 20 parts of ultramarine, 4 parts of iron oxide, 3 parts of yellow iron oxide, 8 parts of carbon black, 20 parts of polyethylene wax, 5 parts of calcium stearate 5 parts of magnesium stearate, 2.2 parts of Polymer-bonded antistatic agent No. 1 and 1.0 part of a 20% polyethylene master batch of Polymer-bonded antioxidant No. 1 were processed into a homogeneous compound in a high-speed mixer, and through an extruder, the compound was extruded at 180° C., whereby a pellet-like coloring master batch was obtained.

Compounded next in a tumbler were 100 parts of a composite material for molded components for use in automotive vehicles, said composite material containing a resin component composed of polypropylene, ethylene-propylene rubber and isotactic polypropylene and also containing 20% of talc, 3 parts of the pigment master batch obtained in the above, 2.2 parts of a 20% polyethylene master batch of Polymer-bonded antioxidant No. 1, 3.4 parts of a 20% polyethylene master batch of Polymer-bonded light stabilizer No. 1, and 0.1 part of calcium stearate. The resulting compound was molded at a molding temperature of 220° C. and a back pressure of 15 kg/cm$^2$ by an injection molding machine. Test pieces so obtained showed sufficiently good results in physical property tests such as a tensile test, a bending test, an Izod impact strength test, a tensile elongation test and a flexural modulus test. Those test pieces were uniformly colored, and were also found to be fully satisfactory in durability such as occurrence of cracks in an accelerated weathering test and heat deterioration time in a heat resistance test.

Master batches were likewise obtained by using Polymer-bonded antistatic agent No. 2, Polymer-bonded antioxidants Nos. 2 to 6 and Polymer-bonded light stabilizers Nos. 2 to 4 in place of Polymer-bonded antistatic agent No. 1, Polymer-bonded antioxidant No. 1 and Polymer-bonded light stabilizer No. 1 employed in the above. These polymer-bonded functional agents also provided molded products of improved physical properties.

EXAMPLE 10

A surface-coating resin formulation for steel plates was prepared by mixing and dissolving 140 parts of a carboxyl-containing thermosetting acrylic resin (acid value as measured in the form of a varnish: 10, solid content: 40%, solvent: "Solvesso #100"/n-butanol (85:15) mixed solvent), 50 parts of a methoxymethylmelamine resin (solid content: 60%, solvent: methanol/isopropanol/isobutanol: 50/35/15), 40 parts of a mixed solvent of "Solvesso #100"/n-butanol (85:15), 6.5 parts of Polymer-bonded ultraviolet absorber No. 3 and 2.0 parts of Polymer-bonded light stabilizer No. 2. The surface-coating resin formulation was applied to a steel plate which had been treated for the prevention of rusting and applied with an undercoat. After the thus-applied surface-coating resin formulation was dried, its curing was conducted at 140° C. for 30 minutes. A weathering test of the thus-formed coating was conducted by a "Sunshine Weather-O-Meter" (trade mark). The coating showed a high percentage of gloss retention for a long time, so that excellent effect was demonstrated.

EXAMPLE 11

An acrylic lacquer enamel was prepared by mixing and dissolving 100 parts of a thermoplastic acrylic resin (solid content: 40%, toluene/n-butanol: 97/3), 5 parts of copper phthalocyanine blue pigment, 4.0 parts of Polymer-bonded ultraviolet absorber No. 2, 2.9 parts of Polymer-bonded light stabilizer No. 4, 20.0 parts of toluene, 10.0 parts of xylene, 6.0 parts of n-butanol and 2.1 parts of propylene glycol monomethyl ether acetate. The acrylic lacquer enamel was applied to a polycarbonate plate. The thus-applied acrylic lacquer enamel was dried in air at room temperature for 30 minutes and then dried under heat at 120° C. for 30 minutes. A polycarbonate plate coated in a beautiful blue color was obtained. A weathering test was also conducted by a "Sunshine Weather-O-Meter" (trade mark). The polycarbonate plate was found to have very improved yellowing resistance.

EXAMPLE 12

An ultraviolet curing, urethane-based coating formulation was prepared by adding 66.7 parts of a polyester diol (a co-condensation polyester diol of terephthalic acid-sebacic acid-ethylene glycol-neopentyl glycol, average molecular weight: 2,000) to 87.2 parts of a mixed solvent of toluene/methyl ethyl ketone (8:2), 19.2 parts of hydroxypropyl methacrylate, 0.1 part of dioctyltin-dilaurate and 2.2 parts of diethoxyacetophenone, thoroughly stirring and mixing them, and then causing 22.2 parts of isophorone diisocyanate to react. To the ultraviolet curing, urethane-based coating formulation, 0.7 parts of Polymer-bonded antioxidant No. 1 and 1.7 parts of Polymer-bonded light stabilizer No. 1 were added, followed by stirring and mixing. The resulting formulation was coated as an ultraviolet curing adhesive on a polyester film, and the thus-coated formulation was dried. The polyester film so coated was compression-bonded under heat with another polyester film, to which ultraviolet rays were irradiated for 10 seconds by an ultraviolet lamp to cure the adhesive. The adhesive showed excellent adhesion and also superb light resistance.

EXAMPLE 13

A two-pack coating formulation was obtained by combining 100 parts of polyethylene adipate polyol (average molecular weight: 2,000) as a primary material of a coating composition for molded products of ABS, 3.4 parts of Polymer-bonded ultraviolet absorber No. 1, 1.7 parts of Polymer-bonded light stabilizer No. 1, 20 parts of wet-process silica (primary particle size: 24 nm), 150 parts of butyl acetate and 40 parts of xylol and then stirring the resultant mixture. To the mixture, 1 part of polyhexamethylene carbodiimide hydrolysis preventive and 20 parts of a 75% solution of a hexamethylene-diisocyanate-type polyisocyanate containing biuret bonds (solvent: ethyl acetate/xylene=1/1) were added to obtain a two-pack coating formulation. The two-pack coating formulation was applied onto a molded product of ABS by a spray gun at an atomization pressure of 4 kg/cm² to give a dry coating thickness of 40 µm. The thus-applied coating formulation was forced to dry with hot air of 80° C. for 30 minutes, whereby a coating of excellent rubbery touch feeling was obtained.

EXAMPLE 14

20 Parts of a carboxyl-containing vinyl chloride-vinyl acetate copolymer, 1.0 part of Polymer-bonded ultraviolet absorber No. 1 and 0.6 part of Polymer-bonded light stabilizer were dissolved in 70 parts of a mixed solvent of butyl acetate-methyl isobutyl ketone-xylene (43:20:37). Separately added to portions of the thus-obtained solution were 9 parts of copper phthalocyanine blue pigment as a blue color, 10 parts of dimethyl quinacridone pigment as a red color, 11 parts of a yellow polyazo pigment as a yellow color, and 8 parts of carbon black pigment as a black color. The thus-prepared mixtures were separately charged in ball mills, followed by dispersion for 16 hours. 3 Parts of silica were added to and mixed with 97 parts of each dispersion, to which 2.7 parts of a 75% solution of a hexamethylene-diisocyanate-type polyisocyanate having a biuret bond were added, followed by mixing. Blue, red, yellow and black ink compositions were hence obtained. Using those ink compositions, patterns were printed by a gravure printing process on a surface of a semi-hard vinyl chloride film. Drying of the colorant inks was conducted at room temperature, and aging was then conducted in a constant-temperature chamber of 30 to 40° C. A polyvinyl chloride sheet was obtained with a printed pattern of 4 colors. The pattern showed excellent weatherability.

What is claimed is:

1. A master batch obtained by blending and kneading at least one polymer-bonded functional agent and at least one polymer and forming said master batch in a sheet form or a pellet form so that said master batch contains the moieties of the functional agent at a concentration of 5 to 20% by weight, as calculated in terms of functional agent moieties, wherein the polymer-bonded functional agent is obtained by the esterification of an ethylene-vinyl alcohol copolymer or an ethylene-vinyl alcohol-vinyl acetate terpolymer containing hydroxy group(s) as the reactive group(s) with a functional agent containing acid halide group(s) as the reactive group(s), wherein the functional agent comprises at least one functional agent selected from the group consisting of antioxidants, ultraviolet absorbers, light stabilizers, infrared absorbers and antistatic agents, and the polymer-bonded functional agent contains the moieties of the functional agent at a concentration of 22 to 55% by weight, as calculated in terms of functional agent moieties.

2. The master batch according to claim 1, wherein the polymer of the polymer-bonded functional agent is an ethylene-vinyl alcohol copolymer or an ethylene-vinyl alcohol-vinyl acetate terpolymer and the functional agent is an acid halide of $3\text{-}[3^1\text{-}(2^{11}\text{-H-benzotriazol-}2^{11}\text{-yl})\text{-}4\text{-hydroxyphenyl}]$ propionic acid.

3. A master batch obtained by blending and kneading at least one polymer-bonded functional agent and at least one polymer and forming said master batch in a sheet form or a pellet form so that said master batch contains the moieties of the functional agent at a concentration of 5 to 20% by weight, as calculated in terms of functional agent moieties, wherein the polymer-bonded functional agent is obtained by the esterification of ethylene-vinyl alcohol copolymer or an ethylene-vinyl alcohol-acetate terpolymer containing hydroxy group(s) as the reactive group(s) with a functional agent of a lower ($C_1$–$C_3$) alkyl ester or an acid halide of at least one selected from the group consisting of 3-(3',5'-di-t-butyl-4'-hydroxyphenyl)propionic acid, 3-(3'-t-butyl-5'-methyl-4'-hydroxyphenyl)propionic acid, 3,5-di-t-butyl-4-hydroxybenzoic acid, 3-[3'-(2"H-benzotriazol-2"-yl)-4'-hydroxyphenyl)]propionic acid, 3-[3'-(2"H-benzotriazol-2"-yl)-5'-methyl-4'-hydroxyphenyl]propionic acid, 3-[3'-(2"H-benzotriazol-2"-yl)-5'-ethyl-4'-hydroxyphenyl]propionic acid, 3-[3-(2"H-benzo-triazol-2"-yl)-5'-t-butyl-4'-hydroxyphenyl]propionic acid, 3-[3'-(5"-chloro-2"H-benzotriazol-2"-yl)-5'-t-butyl-4'-hydroxyphenyl]propionic acid, 3-[3"-(2"H-benzotriazol-2'"-yl)-4"-hydroxy-5"-(1',1'-dimethylbenzyl)phenyl]propionic acid, and 3-[3"-(2'"H-benzotriazol-2'"-yl)-4"-hydroxy-5"-(1",3",3"-tetramethylbutyl)phenyl]propionic acid.

4. The master batch accord to claim 3, wherein the functional agent is a lower ($C_1$–$C_3$) alkyl ester of 3-[3'-(2"-H-benzotriazol-2"-yl)-4-hydroxyphenyl]propionic acid.

5. The mater batch according to claim 3, wherein the functional agent is an acid halide of at least one selected from the group consisting of 3-(3',5'-di-t-butyl-4'-hydroxyphenyl)propionic acid, 3-(3'-t-butyl-5'-methyl-4'-hydroxyphenyl)propionic acid, 3,5-di-t-butyl-4-hydroxybenzoic acid, 3-[3'-(2"H-benzotriazol-2"-yl)-4'-hydroxyphenyl)]propionic acid, 3-[3'-(2"H-benzotriazol-2"-yl)-5'-methyl-4'-hydroxyphenyl]propionic acid, 3-[3'-(2"H-benzotriazol-2"-yl)-5'-ethyl-4'-hydroxyphenyl]propionic acid, 3-[3-(2"H-benzo-triazol-2"-yl)-5'-t-butyl-4'-hydroxyphenyl]propionic acid, 3-[3'-(5"-chloro-2"H-benzotriazol-2"-yl)-5'-t-butyl-4'-hydroxyphenyl]propionic acid, 3-[3"-(2"H-benzotriazol-2'"-yl)-4"-hydroxy-5"-(1',1'-dimethybenzyl)phenyl]propionic acid, and 3-[3"-(2'"H-benzotriazol-2'"-yl)-4"-hydroxy-5"-(1",1",3",3"-tetramethylbutyl)phenyl]propionic acid.

6. The master batch according to claim 3, wherein the functional agent is a lower ($C_1$–$C_3$) alkyl ester of at least one selected from the group consisting of 3-(3',5'-di-t-butyl-4'-hydroxyphenyl)propionic acid, 3-(3'-t-butyl-5'-methyl-4'-hydroxyphenyl)propionic acid, 3,5-di-t-butyl-4-hydroxybenzoic acid, 3-[3'-(2"H-benzotriazol-2"-yl)-4'-hydroxyphenyl)]propionic acid, 3-[3'-(2"H-benzotriazol-2"-yl)-5'-methyl-4'-hydroxy-phenyl]propionic acid, 3-[3'-(2"H-benzotriazol-2"-yl)-5'-ethyl-4'-hydroxyphenyl]propionic acid, 3-[3"-(2"H-benzo-triazol-2"-yl)-5'-t-butyl-4'-hydroxyphenyl]propionic acid, 3-[3'-(5"-chloro-2"H- benzotriazol-2"-yl)-5'-t-butyl-4'-hydroxyphenyl]propionic acid, 3-[3"-(2'"H-benzotriazol-2'"-yl)-4"-hydroxy-5"-(1',1'-dimethybenzyl)phenyl]propionic acid, and 3-[3"-(2'"H-benzotriazol-2'"-yl)-4"-hydroxy-5"-(1",1",3",3"-tetramethylbutyl)phenyl]propionic acid.

* * * * *